(12) United States Patent
Abrams

(10) Patent No.: US 8,137,319 B2
(45) Date of Patent: Mar. 20, 2012

(54) ACCESS PORT INCLUDING CENTERING FEATURE

(75) Inventor: Michael E. Abrams, New York, NY (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/717,286

(22) Filed: Mar. 4, 2010

(65) Prior Publication Data

US 2010/0241079 A1   Sep. 23, 2010

Related U.S. Application Data

(60) Provisional application No. 61/161,814, filed on Mar. 20, 2009.

(51) Int. Cl.
  *A61B 17/34* (2006.01)
(52) U.S. Cl. ............... 604/167.01; 604/164.12; 604/264
(58) Field of Classification Search ........... 604/164.01–164.05, 165.01–165.02, 604/167.01–167.04, 167.06, 264, 506, 164.07, 604/164.12; 606/108, 167, 185
  See application file for complete search history.

(56) References Cited

U.S. PATENT DOCUMENTS

| | | | |
|---|---|---|---|
| 5,308,336 A * | 5/1994 | Hart et al. ................ | 604/167.03 |
| 5,662,615 A | 9/1997 | Blake, III | |
| 6,238,407 B1 * | 5/2001 | Wolf et al. .................... | 606/185 |
| 2008/0097332 A1 | 4/2008 | Greenhalgh et al. | |
| 2008/0294125 A1 | 11/2008 | Focht et al. | |

FOREIGN PATENT DOCUMENTS

| | | |
|---|---|---|
| EP | 0538060 | 4/1993 |
| EP | 1637178 | 3/2006 |

OTHER PUBLICATIONS

European Search Report for EP 10 25 0520 date of completion is Jun. 23, 2010 (3 pages).

* cited by examiner

*Primary Examiner* — Quynh-Nhu H Vu

(57) ABSTRACT

A surgical access port includes an access member defining a longitudinal axis and having an interior wall defining a longitudinal opening adapted for passage of a surgical object, an object seal disposed in mechanical cooperation with the access member and configured to create a substantially fluid-tight seal around a surgical object inserted through the object seal and a centering mechanism mounted to the access member proximal of the object seal. The centering mechanism includes at least one centering element extending at least in a general longitudinal direction within the longitudinal opening, and defining proximal and distal longitudinal end segments. The at least one centering element is positioned and dimensioned to engage the surgical object during passage of the object through the longitudinal opening to normally bias the surgical object into general alignment with the longitudinal axis. A locking member is mounted to the distal longitudinal end segment of the at least one centering element. The locking member is adapted for longitudinal movement relative to the longitudinal axis when the surgical object is in generally aligned relation with the longitudinal axis. The locking member is dimensioned to engage the interior wall of the access member upon asymmetrical manipulation of the surgical object relative to the longitudinal axis to substantially lock the centering mechanism and prevent further asymmetrical manipulation of the surgical object until the surgical object is returned to the generally aligned relation with the longitudinal axis under the bias of the at least one centering element.

14 Claims, 3 Drawing Sheets

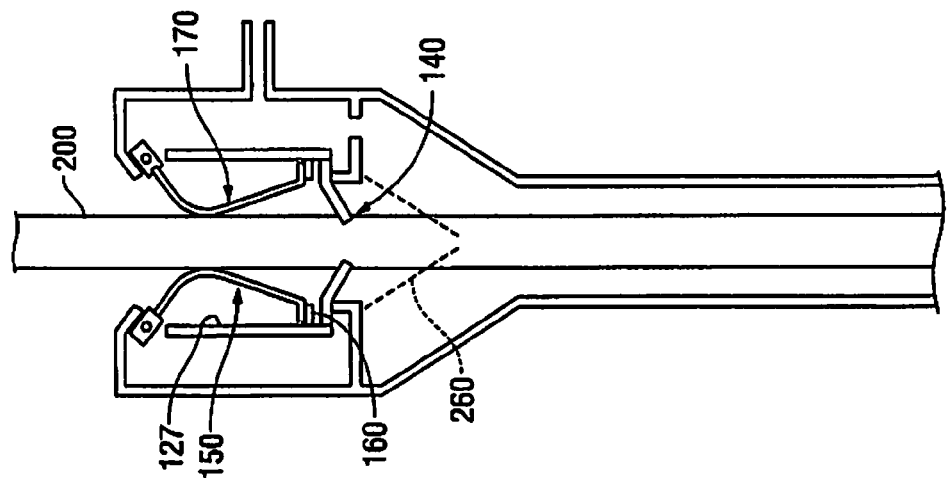
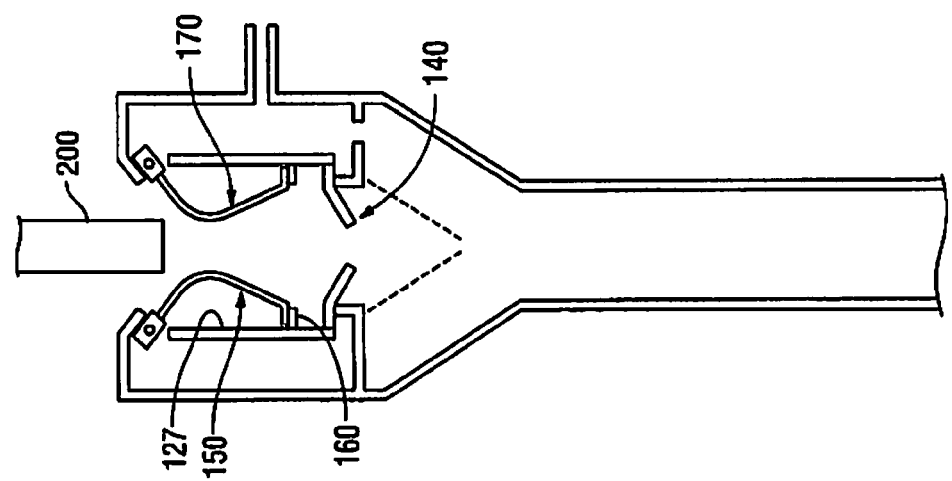

ACCESS PORT INCLUDING CENTERING FEATURE

CROSS REFERENCE TO RELATED APPLICATION

The present application claims the benefit of and priority to U.S. Provisional Application Ser. No. 61/161,814 filed on Mar. 20, 2009, the entire contents of which are incorporated herein by reference.

BACKGROUND

1. Technical Field

The present disclosure relates to an access port which is adapted to allow the introduction of surgical instrumentation into a patient's body.

2. Description of the Related Art

In laparoscopic procedures, surgery is performed in the interior of the abdomen through a small incision; in endoscopic procedures, surgery is performed in any hollow viscus of the body through a narrow tube or cannula inserted through a small entrance incision in the skin. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. Moreover, laparoscopic and endoscopic procedures often require the surgeon to act on organs, tissue, and vessels far removed from the incision, thereby requiring that any instruments used in such procedures be relatively long and narrow.

For such procedures, the introduction of a tube into certain anatomical cavities such as the abdominal cavity is usually accomplished by use of a trocar assembly including a cannula assembly and an obturator assembly. Since the cannula assembly provides a direct passage for surgical instrumentation from outside the patient's body to access internal organs and tissue, it is important that the cannula assembly maintain a relatively gas-tight interface between the abdominal cavity and the outside atmosphere. The cannula assembly generally includes a cannula attached to a cannula housing containing a seal assembly adapted to maintain a seal across the opening of the cannula housing.

Since surgical procedures in the abdominal cavity of the body require insufflating gases to raise the cavity wall away from vital organs, the procedure is usually initiated by use of a Verres needle through which a gas such as $CO_2$ is introduced into the body cavity, thereby creating a pneumoperitoneum. The gas provides a positive pressure which raises the inner body wall away from internal organs, thereby providing the surgeon with a region within which to operate and avoiding unnecessary contact with the organs by the instruments inserted through the cannula assembly. An obturator of the obturator assembly is inserted into the cannula assembly and used to puncture the abdominal wall. Following removal of the obturator assembly from the cannula assembly, laparoscopic or endoscopic surgical instruments may be inserted through the cannula assembly to perform surgery within the abdominal cavity.

Generally in the context of insufflatory surgical procedures, there are two sealing requirements for cannula assemblies. The first requirement is to provide a substantially fluid-tight seal when an instrument is not being introduced into or is not already present in the cannula. The second requirement is to provide a substantially fluid-tight seal when an instrument is being introduced into or is already present in the cannula. Additionally, as endoscopic and laparoscopic surgical procedures and techniques have advanced, it has become desirable to accommodate surgical instrumentation of varying outside diameters through a single cannula assembly in a given surgical procedure, thereby minimizing the number of cannula required and facilitating efficiency in the surgical procedure.

SUMMARY

In accordance with a preferred embodiment, a surgical access port includes an access member defining a longitudinal axis and having an interior wall defining a longitudinal opening adapted for passage of a surgical object, an object seal disposed in mechanical cooperation with the access member and configured to create a substantially fluid-tight seal around a surgical object inserted through the object seal and a centering mechanism mounted to the access member proximal of the object seal. The centering mechanism includes at least one centering element extending at least in a general longitudinal direction within the longitudinal opening, and defining proximal and distal longitudinal end segments. The at least one centering element is positioned and dimensioned to engage the surgical object during passage of the object through the longitudinal opening to normally bias the surgical object into general alignment with the longitudinal axis. A locking member is mounted to the distal longitudinal end segment of the at least one centering element. The locking member is adapted for longitudinal movement relative to the longitudinal axis when the surgical object is in generally aligned relation with the longitudinal axis. The locking member is dimensioned to engage the interior wall of the access member upon asymmetrical manipulation of the surgical object relative to the longitudinal axis to substantially lock the centering mechanism and prevent further asymmetrical manipulation of the surgical object until the surgical object is returned to the generally aligned relation with the longitudinal axis under the bias of the at least one centering element.

The centering mechanism may include a plurality of centering elements. Each centering element has a proximal longitudinal end segment and a distal longitudinal end segment mounted to the locking member. The proximal longitudinal ends of the centering elements may be secured to the access member. The centering elements may be coaxially arranged about the longitudinal axis. The centering elements may be each dimensioned to have an intermediate bow segment between the proximal and distal end segments with the bow segment defining a substantially curved configuration.

The locking member may be substantially annular. In one embodiment, the locking member is dimensioned to engage the interior wall upon offset manipulation of the surgical object and is substantially prevented from further longitudinal movement until the surgical object is returned to the generally aligned relation with the longitudinal axis under the bias of the centering elements. The object seal may define a substantially conical segment and be disposed distal of the centering elements.

In another embodiment, a surgical cannula assembly includes a cannula housing having an internal wall defining an internal chamber, a cannula member extending from the cannula housing and having a longitudinal opening in alignment with the internal chamber of the cannula housing for reception and passage of a surgical object, a plurality of centering elements mounted to the cannula housing and defining a central axis, an object seal configured to create a substantially fluid-tight seal around the surgical object and a substantially annular locking member mounted to the centering elements. The centering elements include proximal and distal longitudinal end segments and are at least partially disposed within the internal chamber. The centering elements are positioned and dimensioned to engage the surgical object during passage of the object through the longitudinal opening and are capable of radial outward deflective movement relative to the longitudinal axis from an initial position to a radial outward position in response to an outward force exerted by the surgical object. The centering elements may be normally biased toward the initial position to bias the surgical object toward a generally aligned position with respect to the central axis. The annular locking member is dimensioned to engage the interior wall upon asymmetrical manipulation of the surgical object to substantially minimize further manipulation of the surgical object until the surgical object is returned to the generally aligned relation with the central axis under the bias of the centering elements.

The locking member may be adapted to move in a longitudinal direction relative to the longitudinal axis when the surgical object is in general longitudinal alignment with the central axis of the centering elements. The locking member may be adapted to engage the internal wall of the cannula housing upon asymmetrical manipulation of the surgical object and is substantially prevented from further longitudinal movement until the surgical object is returned to the generally aligned relation with the central axis under the bias of the centering elements. The central axis of the centering elements may be in general alignment with the longitudinal axis of the cannula member. The object seal may be disposed distal of the centering elements.

BRIEF DESCRIPTION OF THE DRAWINGS

Various embodiments of the present disclosure are described herein with reference to the drawings wherein:

FIG. 5 is a longitudinal cross-sectional view of the access port illustrating a wide surgical instrument prior to insertion into the access port and being substantially aligned with the longitudinal axis of the access portion; and FIG. 6 is a view similar to the view of FIG. 5 illustrating the wide surgical instrument advanced within the access port.

DETAILED DESCRIPTION

The access port of the present disclosure, either alone or in combination with a cannula assembly, provides a substantially fluid-tight seal between a body cavity of a patient and the outside atmosphere. The access port of the present disclosure is configured to receive instruments of varying diameters. The centering mechanism includes centering ribs or elements which assist in maintaining a substantially symmetrical position of a surgical instrument with respect to a longitudinal axis during insertion into the access port or cannula assembly. The centering elements also help maintain the substantially symmetrical position of an instrument disposed within the access port while the instrument is disposed therethrough.

The access port of the present disclosure contemplates the introduction of various types of instrumentation adapted for insertion through a trocar and/or cannula assembly while maintaining a substantially fluid-tight interface about the instrument to help preserve the atmospheric integrity of a surgical procedure from gas and/or fluid leakage. Specifically, the access port includes at least two centering elements which bias an instrument entering the port such that as the instrument enters the port or, the instrument is normally biased toward a substantially symmetrical relation with the longitudinal axis. This feature of the present disclosure minimizes the entry and exit of gases and/or fluids to/from the body cavity.

Examples of instrumentation include, but are not limited to, clip appliers, graspers, dissectors, retractors, staplers, laser probes, photographic devices, endoscopes and laparoscopes, tubes, and the like. Such instruments will collectively be referred to as "instruments" or "instrumentation."

In the following description, as is traditional, the term "proximal" or "trailing" refers to the portion of the device closer to the operator while the term "distal" or "leading" refers to the portion of the device further from the operator.

Figure 1:
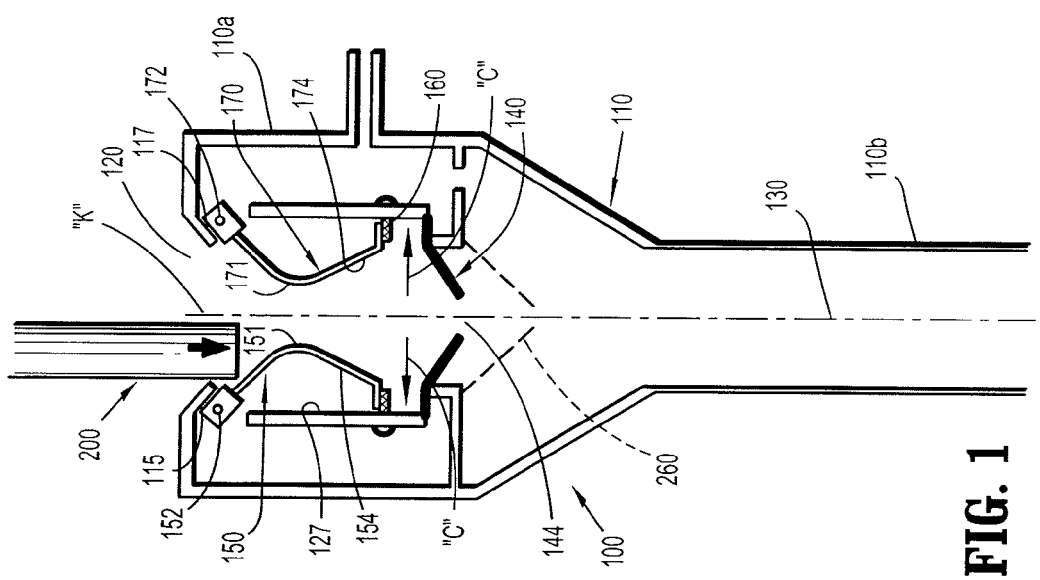
FIG. 1 is a longitudinal cross-sectional view of the access port illustrating the centering elements, locking ring and seal and depicting initial asymmetric insertion of an instrument.

Referring now to the drawings, FIG. 1 illustrates access port 100 including access member 110 defining a longitudinal axis 130. Access member 110 may be a cannula assembly includes a cannula housing 110a and an elongated sleeve or cannula 110b extending from the cannula housing 110a. Housing 110a includes an orifice seal 140 having an aperture 144 therein. Orifice seal 140 may be made from a low durometer elastomer and/or include a hydrophilic coating. Orifice seal 140 may be a conical or tapered seal extending along the longitudinal axis 130. Opposing centering elements or ribs 150, 170 are disposed within housing 110a and may be secured to respective inner surfaces 115, 117 of housing 110a adjacent their respective proximal ends 152, 172. Centering elements 150, 170 may be secured to inner surfaces 115, 117 and may be arranged about central axis "k" of the centering elements 150, 170. Central axis "k" and longitudinal axis 130 may be in general longitudinal alignment. Centering elements 150, 170 are attached to a substantially annular locking ring 160 adjacent their respective distal ends 154, 174. Locking ring 160 may be generally circular, elliptical or any other configuration. Locking ring 160 is free of engagement with housing 110a and moves in a longitudinal direction with respect to the longitudinal axis 130. Locking ring 160 and centering elements 150, 170 are spaced from orifice seal 140 when in the initial position of FIG. 1. Centering elements 150, 170 and ring 160 form a centering mechanism tending to bias the surgical object into general alignment with the longitudinal axis 130 and/or preventing further manipulation of the surgical object until the object is in general alignment with the central axis "k". Centering elements 150, 170 may be formed of any material having sufficient resiliency to permit deflection and return to its initial position. Centering elements 150, 170 may be secured to an internal surface of housing 110 by conventional means including adhesive, cements, pins, fasteners or the like. Ring 160 may be secured to centering elements 150, 170 in a similar manner. Suitable materials for centering elements 150, 170 may include polymeric material, spring steel, titanium or the like. Locking ring 160 may be formed of a more rigid material. Locking ring 160 may define a dimension or diameter substantially approximating the internal dimension of internal wall 127 of housing 110a. Internal wall 127 may define a general circular internal dimension or any other dimension corresponding to the dimension of locking ring 160. In one embodiment, locking ring 160 is generally circular and internal wall 127 defines a generally circular internal dimension.

A distal end 112 of housing 110a is shown monolithically formed with a cannula 110b. Access port 100 may include a second seal 260 (shown in phantom) which provides a substantially fluid-tight seal in the absence of a surgical instrument passing therethrough.

While two centering elements 150 and 170 are shown, it is envisioned and within the scope of the present disclosure that access port 100 includes more (e.g., four centering elements at 90 degree radial intervals) or fewer than two centering elements.

Opposing centering elements 150, 170 may include bow segments 151, 171 in its normal state such that the gap distance between opposing centering elements 150, 170 at its narrowest point is slightly less than the smallest diameter instrument which is likely to be inserted into access member 110. For example, if the minimum diameter instrument which is likely to be introduced into access member 110 is about 5 mm, the gap distance between opposing centering elements 150, 170, at its narrowest point, could be about 4.5 mm in an at-rest position. Opposing centering elements 150, 170 may also be configured such that in a flexed position, opposing centering elements 150, 170 can accommodate instruments having a diameter up to about 12 mm. Thus, access port 100 may be adapted to receive surgical instrumentation having a diameter in the range of about 5 mm to about 12 mm. The capability of access port being adapted to accommodate smaller and larger diameter instruments is also envisioned.

Opposing centering elements 150, 170 and ring 160 cooperate to assist in maintaining a substantially symmetrical relation of a surgical instrument 200 with respect to a longitudinal axis 130, thus, minimizing of leakage of fluids between orifice seal 140 and the object or instrument 200, e.g., once disposed through access member 110, surgical instrument 200 is radially held in place, substantially symmetrical about longitudinal axis 130 via opposing centering elements 150, 170 and ring 160. The operation of centering elements 150, 170 and ring 160 before, during and after insertion of a surgical instrument into access member 110 will be described more fully below.

Figure 2:
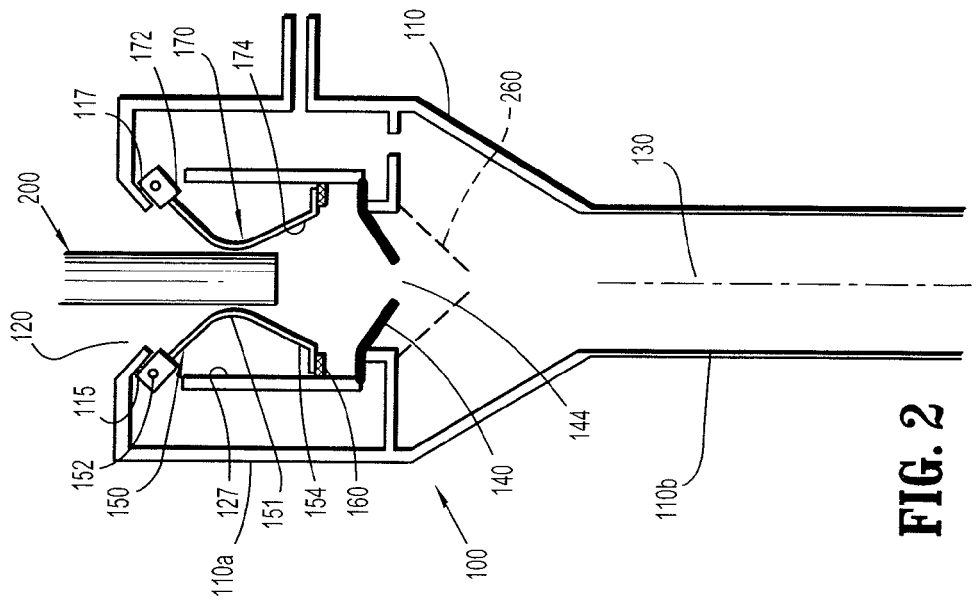
FIG. 2 is a view similar to the view of FIG. 1 illustrating the instrument within the access port and aligned relative to the longitudinal axis of the access port.
Figure 3:
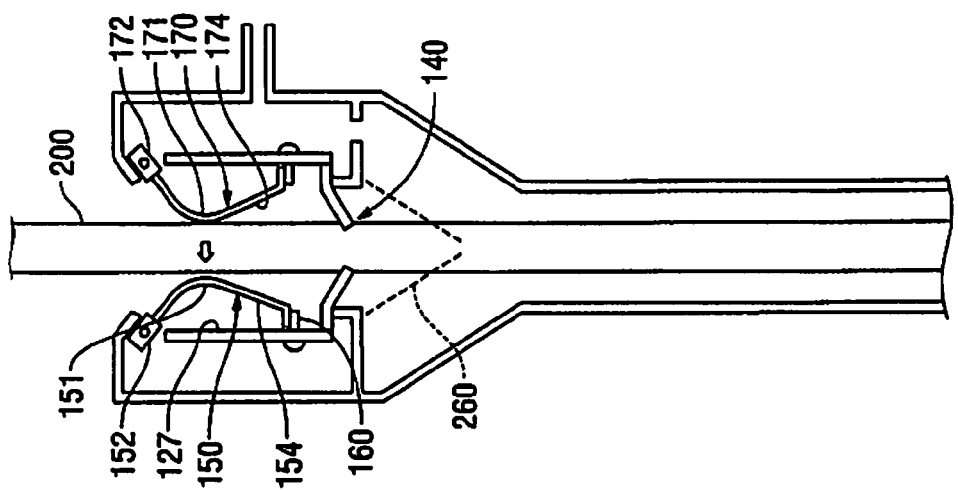
FIG. 3 is a longitudinal cross-sectional view of the access port illustrating angulated manipulation of the instrument within the access port and consequent locking of the locking ring.
Figure 4:
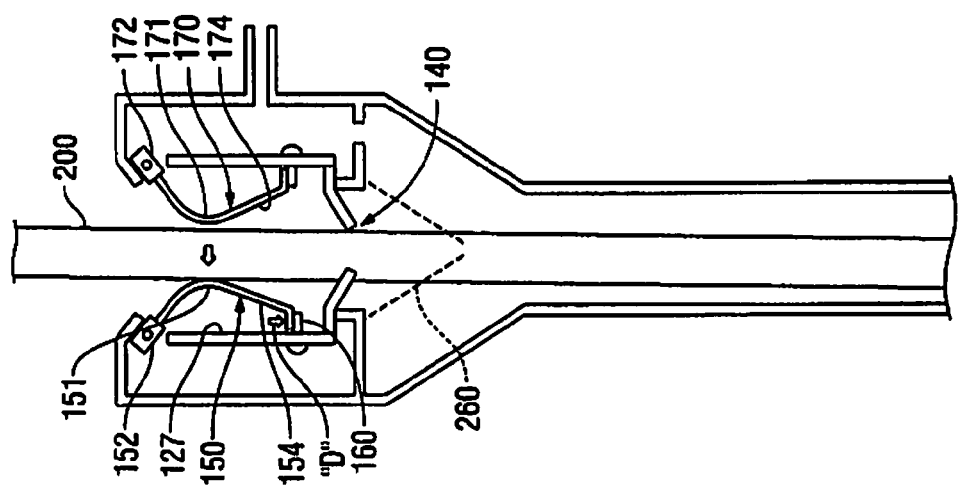
FIG. 4 is a view similar to the view of FIG. 1 illustrating the instrument fully advanced within the access port.

The use of access port 100 will now be described in detail with reference to FIGS. 1-4. FIG. 1 shows instrument 200 being initially introduced into a channel 120 defined within access member 110 of access port 100 in a laterally offset position or asymmetrical manipulation relative to longitudinal axis 130 (arrow A). Asymmetrical may be interpreted as at least including offset, angulated, lateral or the like with respect to the longitudinal axis 130. Before insertion of instrument 200, centering elements 150, 170 and ring 160 are in an initial at-rest position, as shown in FIG. 1. As instrument 200 is further advanced distally in the direction of arrow A, instrument 200 contacts centering element 150. Upon contacting centering element 150, instrument 200 exerts both radial and longitudinal forces force on centering element 150. Since centering element 150 is rigidly attached to inner surface 115 of access member 110 adjacent proximal end 152, the force applied to centering element 150 causes the centering element 150 to bow or deflect in the direction of arrow C which may also cause translation of locking ring 160 in an axial direction of arrow D. If the instrument 200 is in general alignment with central axis "k", locking ring 160 will translate within internal wall 127 of access member 110, and permit further advancing manipulation of the surgical object or instrument 200. However, if the surgical instrument 200 is subject to asymmetrical movement during insertion, advancement or manipulation within the body cavity, this asymmetrical movement will impart a radial force to locking ring 160 driving the locking ring 160 into engagement with internal wall 127. As a result, locking ring 160 is forced into interior wall 127 in the direction of directional arrows "c" (FIG. 1) in secured relation therewith through, e.g., a frictional relationship created between locking ring 160 and inner wall 127 of access member 110. With locking ring 160 secured relative to interior wall 127, the locking ring 160 may no longer translate in, e.g., the axial direction. In this secured relation of locking ring 160, continued asymmetrical movement of the surgical instrument 200 is substantially prevented until the surgical instrument 200 is returned to the generally aligned relation with the central axis "k" under the bias of the centering elements 150, 170. Specifically, a counterforce is created within rib 150, biasing the rib 150 and the surgical instrument or object 200 toward an aligned position with respect to the longitudinal axis 130 as depicted in FIG. 2. Once the surgical object is aligned, the surgical object 200 may be continually advanced through aperture 144 of orifice seal 140 creating a fluid-tight relationship around instrument 200. If alignment is maintained, the surgical object 200 may be advanced with centering elements 150, 170 deflecting to cause corresponding axial movement of locking ring 160. For example, when an even load is applied to centering elements 115, 117 coaxial arrangement of locking ring 160 with respect to central axis "k" is achieved thus permitting the locking ring 160 and instrument 200 to translate in an axial direction. However, if during any time, the surgical object 200 is laterally manipulated or angulated relative to the longitudinal axis 130 as depicted in FIG. 3, centering elements 150 or 170 will deflect causing corresponding radial movement of locking ring 160 into engagement with inner wall 127. In this position depicted in FIG. 3, advancing movement of the surgical object or instrument 200 is substantially prevented until the surgical instrument 200 is in general alignment with the central axis "k", and, equal forces are applied to centering elements 150, 170 whereby the centering elements 150, 170 bias the surgical object 200 into alignment with the central axis "k" as depicted in FIG. 4. With the surgical instrument aligned, the surgical instrument may be advanced to the targeted tissue site to perform the desired surgery.

Locking ring 160 may include a textured outer surface, e.g., such as ribs, protrusions, teeth or the like to facilitate engagement with the interior wall 127 of access member 110. Locking ring 160 may also have an elastomeric outer surface to facilitate frictional engagement with interior wall 127. Interior wall 127 may include similar surfaces.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A surgical access port comprising:
an access member defining a longitudinal axis and having proximal and distal ends, the access member having an interior wall defining a longitudinal opening adapted for passage of a surgical object;
an object seal disposed in mechanical cooperation with the access member, the object seal configured to create a substantially fluid-tight seal around a surgical object inserted through the object seal; and a centering mechanism mounted to the access member proximal of the object seal, the centering mechanism including:

at least one centering element extending at least in a general longitudinal direction within the longitudinal opening, and defining proximal and distal longitudinal end segments, the at least one centering element positioned and dimensioned to engage the surgical object during passage of the surgical object through the longitudinal opening to normally bias the surgical object into general alignment with the longitudinal axis: and a locking member mounted to the distal longitudinal end segment of the at least one centering element, the locking member moves longitudinally relative to the longitudinal axis when the surgical object is in generally aligned relation with the longitudinal axis, the locking member dimensioned to engage the interior wall of the access member upon asymmetrical manipulation of the surgical object relative to the longitudinal axis to substantially lock the centering mechanism and prevent further asymmetrical manipulation of the surgical object until the surgical object is returned to the generally aligned relation with the longitudinal axis under the bias of the at least one centering element; the at least centering element having an intermediate bow segment between the proximal and distal longitudinal end segments, the bow segment defining a substantially curved configuration.

2. The access port of claim 1, including a second centering element, the second centering element having a proximal longitudinal end segment and a distal longitudinal end segment mounted to the locking member.

3. The access port of claim 2, wherein the proximal longitudinal ends of the centering elements are secured to the access member.

4. The access port of claim 3, wherein the centering elements are coaxially arranged about the longitudinal axis.

5. The access port of claim 4, wherein the object seal defines a substantially conical segment.

6. The access port of claim 2, wherein the locking member is substantially annular.

7. The access port of claim 6, wherein the locking member is dimensioned to engage the interior wall upon asymmetrical manipulation of the surgical object and is substantially prevented from further longitudinal movement until the surgical object is returned to the generally aligned relation with the longitudinal axis under the bias of the centering elements.

8. A surgical cannula assembly, which comprises:

a cannula housing including an internal wall defining an internal chamber;

a cannula member extending from the cannula housing, the cannula member defining a longitudinal axis and having a longitudinal opening in alignment with the internal chamber of the cannula housing for reception and passage of a surgical object, the cannula member defining proximal and distal ends;

a plurality of centering elements mounted to the cannula housing and defining a central axis, the centering elements including proximal and distal longitudinal end segments, the centering elements at least partially disposed within the internal chamber, and being positioned and dimensioned to engage the surgical object during passage of the surgical object through the longitudinal opening and being capable of radial outward deflective movement relative to the longitudinal axis from an initial position to a radial outward position in response to an outward force exerted by the surgical object, the centering elements normally biased toward the initial position to bias the surgical object toward a generally aligned position with respect to the central axis;

an object seal configured to create a substantially fluid-tight seal around the surgical object; and a substantially annular locking member mounted to the centering elements, the annular locking member dimensioned to engage the interior wall upon asymmetrical manipulation of the surgical object to substantially minimize further manipulation of the surgical object until the surgical object is returned to the generally aligned relation with the central axis under the bias of the centering elements, the annular locking member moves in a longitudinal direction relative to the longitudinal axis when the surgical object is in general longitudinal alignment with the central axis of the centering elements; the centering elements each having an intermediate bow segment between the proximal and distal longitudinal end segments, the bow segment defining a substantially curved configuration.

9. The surgical cannula assembly according to claim 8, wherein the locking member is adapted to engage the internal wall of the cannula housing upon asymmetrical manipulation of the surgical object and is substantially prevented from further longitudinal movement until the surgical object is returned to the generally aligned relation with the central axis under the bias of the centering elements.

10. The surgical cannula assembly according to claim 9, wherein the central axis of the centering elements is in general alignment with the longitudinal axis of the cannula member.

11. The surgical cannula assembly according to claim 8, wherein the object seal is disposed distal of the centering elements.

12. The access port of claim 1, wherein the locking member is rigid.

13. The surgical cannula assembly of claim 8, wherein the locking member is rigid.

14. The surgical cannula assembly of claim 8, wherein the locking member is longitudinally translatable with respect to the interior wall.

* * * * *